United States Patent
Yang et al.

(10) Patent No.: US 10,619,188 B2
(45) Date of Patent: Apr. 14, 2020

(54) DETECTION OF NUCLEIC ACID SEQUENCES USING ENDONUCLEASE

(71) Applicant: INDUSTRY-ACADEMIC COOPERATION FOUNDATION, YONSEI UNIVERSITY, Seoul (KR)

(72) Inventors: Seong Wook Yang, Seoul (KR); Seok Keun Cho, Goyang-si (KR); Moon Young Ryu, Goyang-si (KR)

(73) Assignee: INDUSTRY-ACADEMIC COOPERATION FOUNDATION, Yonsei University, Seoul ( * ) Notice: Subject to any disclaimer, the term of this patent is extended or adjusted under 35 U.S.C. 154(b) by 0 days.

(21) Appl. No.: 15/474,270

(22) Filed: Mar. 30, 2017

(65) Prior Publication Data
US 2017/0283857 A1 Oct. 5, 2017

(30) Foreign Application Priority Data
Mar. 30, 2016 (KR) .................. 10-2016-0038554

(51) Int. Cl.
*C12Q 1/6806* (2018.01)
*C12N 15/63* (2006.01)
*C12N 9/22* (2006.01)
*C12Q 1/6832* (2018.01)

(52) U.S. Cl.
CPC ............ *C12Q 1/6806* (2013.01); *C12N 9/22* (2013.01); *C12N 15/63* (2013.01); *C12Q 1/6832* (2013.01)

(58) Field of Classification Search
CPC .... C12Q 1/6806; C12Q 1/6832; C12N 15/63; C12N 9/22
See application file for complete search history.

(56) References Cited

PUBLICATIONS

Coulon et al. Molecular Biology of the Cell. 2004. 15:71-80. (Year: 2004).*
Gaur et al. Cell Reports. 2015. 10:1467-1476. (Year: 2015).*
GenBank CAB76036.1—"structure-specific endonuclease catalytic subunit [Schizosaccharomyces pombe]" (Feb. 27, 2015). Retrieved on Jun. 14, 2018 from the internet: https://www.ncbi.nlm.nih.gov/protein/CAB76036.1. (Year: 2015).*
GenBank 4XM5_A—"Chain A, C. Glabrata Slx1." (May 20, 2015). Retrieved on Jun. 14, 2018 from the internet: https://www.ncbi.nlm.nih.gov/protein/783283269. (Year: 2015).*
GenBank NP_180594 (Jan. 22, 2014). Retrieved on Jun. 20, 2018 from the internet: https://www.ncbi.nlm.nih.gov/protein/42569467?sat=46&satkey=37004846. (Year: 2014).*

* cited by examiner

*Primary Examiner* — Joseph G. Dauner
(74) *Attorney, Agent, or Firm* — H.C. Park & Associates, PLC

(57) ABSTRACT

Cloning vectors encoding endonuclease capable of removing false positives. Attempts to diagnose and/or select appropriate treatment methods via genetic screening can be rendered inaccurate do the presence of false positive. The error causing false positives may include double-stranded nucleic acids comprising a bulge and/or Y-junction. Expression vectors encoding an endonuclease capable of removing such error causing false positives are disclosed, along with methods of utilizing the encoded endonucleases to increase diagnostic accuracy and permit selection of more appropriate treatments.

4 Claims, 11 Drawing Sheets
(3 of 11 Drawing Sheet(s) Filed in Color)
Specification includes a Sequence Listing.

DETECTION OF NUCLEIC ACID SEQUENCES USING ENDONUCLEASE

CROSS-REFERENCE TO RELATED APPLICATION

This application claims priority from and the benefit of Korean Patent Application No. 2016-0038554, filed on Mar. 30, 2016, which is hereby incorporated by reference for all purposes as if fully set forth herein.

SEQUENCE LISTING

This application includes a sequence listing filed electronically via the USPTO EFS-WEB server. The entire content of the sequence listings is hereby incorporated by reference into the specification of this application. The sequence listing is identified by the electronically filed ASII (.txt) text files as follows:

| File Name | Date of Creation | Size |
|---|---|---|
| P7178US00_SEQLIST | May 16, 2017 | 4,055 bytes |

BACKGROUND

Field

Exemplary embodiments relate to cloning vectors encoding an endonuclease and detection methods utilizing the endonuclease to remove false positives.

Discussion of the Background

MicroRNA (miRNA) is an important class of regulatory RNA controlling a wide range of biological processes. MicroRNA, like the other RNA molecules within the cell, play a role in making proteins. Everything that occurs within the body, from muscle movement, beating of the heart, and thought, is coordinated by many proteins acting together. Not surprisingly, a failure of proteins to operate correctly is believed to be cause of many diseases. Viruses, for instance, infect cells by hijacking protein production. When a virus enters a cell, it tricks the cell into making proteins that the virus needs to survive and replicate. Other diseases are believed to be due to a lack or excess of certain proteins. Excessive production of amyloid protein plaques, for instance, is believed to be related to Alzheimer's disease. Accordingly, loss of the ability to manage protein production is believed be a cause of many diseases.

Proteins are generally made by ribosomes (another protein) reading instructions provided on messenger RNA (mRNA) to manufacture new proteins. Accordingly, messenger RNA carries to ribosomes the basic blueprints of the proteins to be manufactured. Messenger RNAs are single nucleic acid strands. The instructions for proteins are written on these strands in a chemical language. Ribosomes clamp onto messenger RNAs and slide down then to read the chemical language. As a ribosome reads the chemical language, it builds a protein.

Unlike messenger RNA molecules, miRNA does not carry the blueprints for proteins. Rather, these small non-coding RNA molecules influence protein production. Controlling protein production, miRNA are like molecule foremen within a cell, ensuring that the proper proteins are made at the proper time. MicroRNA may control protein production by binding to and shutting down ribosomes. In some instances, miRNA may control protein production by intercepting mRNA messages and tagging them for deletion. It also suspected that miRNA control protein production by stopping the production of mRNA.

Not carrying instructions for proteins, miRNA are short single-stranded molecules, approximately 21 to 22 nucleotides in length. Though small, miRNA are capable of complementary base pair binding with mRNA carrying the instructions for proteins to be produced. During complementary base pair biding, nucleic acid strands, such as RNA and DNA, bind together to form a double-stranded nucleic acid. In order for the two strands to bind together, they must have matching, i.e. complimentary, sequences.

It is believed that miRNA binding to complimentary sequences on mRNA marks the mRNA for degradation or otherwise inhibits a ribosome from reading the mRNA to make a protein.

Over 2,500 miRNAs have been identified in the human genome. Any given miRNA may target one or more mRNAs. Also, any given mRNA may be targeted by different miRNAs. The binding of multiple miRNAs to single mRNA may induce a synergistic effect.

Playing an important regulatory role in protein production, miRNA help to control various cellular processes, such as differentiation (i.e. making sure a cell becomes a skin cell vs. a bone cell), proliferation (i.e. reproduction), apoptosis (i.e. cell death), metabolic homeostasis (i.e. turning cells on or off), oncogenesis (i.e. formation of tumors), and DNA methylation (i.e. stopping the production of mRNA) (Li H, et al., Hypertension 2003; 42(5): 895-900), miRNA may underlie various diseases. Therefore, the analysis of miRNA expression may provide important diagnostic information. For example, the presence of particular miRNA may indicate a genetic disease. As it is suspected that various viruses utilize miRNAs to infect cells by hijacking protein production, the presence of particular miRNA may diagnose various infections. As such, identifying the miRNA present may assist doctors in selecting the appropriate method of treatment.

Generally, a nucleic acid strand, such as miRNA, is detected within a sample through the use of a probe. The probe contains a nucleic acid stand complimentary to the strand to be detected. This permits the probe to selectively bind to the nucleic acid to be detected, creating a double-stranded nucleic acid complex. In some instances, one strand of this double-stranded complex may contain a label so its presence can be detected. For example, Northern blots use labeled probes to detect the presence of specific RNA molecules within a sample. Typically, a Northern blot begins by separating RNA molecules extracted from a tissue or other sample based on size using gel electrophoresis. A membrane is then placed upon the gel. Clinging to the membrane, RNA molecules are picked up from the gel when the membrane is removed. Depending on the affinity of the RNA molecules to the membrane used, the RNA molecules may then be fixed to the membrane. After assuring that the RNA molecules from the tissue are sufficiently stuck to the membrane, the membrane is exposed to labeled probes. Generally containing a specific sequence of nucleotides, the labeled probes selectively bind to RNA stuck onto the membrane having a matching nucleotide sequence. When the probes bind to their match, a double-stranded nucleic acid results. After giving the probes sufficient time to find and bind to their match on the membrane, the membrane is washed to remove unbound probes. The double-stranded nucleic acids containing the probes remaining on the membrane are then detected using the probes' labels.

Another widely used technique is Southern blots. Similar to the Northern blot technique, Southern blots also use labeled probes to detect the presence of a nucleic acid within a sample. However, rather than RNA, Southern blots detect the presence of DNA within a sample having a specific nucleotide sequence.

Fluorescence in situ hybridization (FISH) is another commonly used technique to detect the presence of a nucleotide sequence within a sample. However, unlike Northern and Southern blots, the nucleotide sequence to be detected is not fixed to a membrane after gel electrophoresis, but rather a different surface. The FISH technique detects nucleotides having a specific sequence within cells or another sample fixed to surface. Accordingly, the FISH technique may begin be adhering the sample to a glass slide. If necessary, double-stranded nucleotides are separated (i.e. denatured) into single strands. Then, as with the Northern and Southern blots, the surface is exposed to labeled probes. As with the previous techniques, when the probes bind to their match, double-stranded nucleic acids results. After giving the probes sufficient time to find and bind to their match on the surface, the surface is washed to remove unbound probes. The double-stranded nucleic acids containing the probes remaining on the membrane are then detected using the probes' labels.

Another commonly used technique to detect the presence of a specific RNA, DNA or other nucleotide sequence is microarray analysis. Using a labeled sample, microarray analysis differs from FISH, Southern blot and Northern blot techniques. Generally, microarray analysis begins by extracting DNA or RNA from a source to be study or examined. The extracted RNA is first used to create cDNA strands through reverse transcription. This initial cDNA may be labeled as to provide a labeled sample. In other instances, a labeled sample may be generated by creating labeled DNA copies of the initial RNA and/or cDNA using polymerase chain reaction (PCR) or other nucleotide amplification techniques. For example, if DNA were extracted rather than RNA, then reverse transcription may be omitted and an amplification of the extracted DNA may be performed to generate a labeled sample. The labeled sample is then exposed to probes fixed to a surface. As with the previous techniques, the nucleotides within the sample bind to matching probes, creating double-stranded nucleic acids. After giving the single-stranded nucleotides within the sample time to find and bind to their matches on the surface, the surface is washed to remove unbound single strands. The double-stranded nucleic acids containing the single strands from the sample remaining on the surface are then detected using the label.

The previously mentioned techniques rely on visible labels. These labels may be in the form of the fluorescent markers that emit light. In other instances, the labels may be visible by x-ray analysis. Regardless, of how the labels are made visible, it is the presence of the label in double-stranded nucleic acids that is detected.

Other techniques may detect the presence of double-stranded nucleic acids by other means. For instance, selective amplification of single-stranded nucleic acids within the sample may be used to detect the presence of double-stranded nucleic acids. This can be accomplished by utilizing a PCR technique that selectively amplifies specific single-stranded nucleotides within the sample. During amplification, a DNA polymerase binds to single-stranded DNA and makes a complimentary copy of the strand. DNA polymerase, however, is incapable of binding to the strand on its own. The help of a primer is required. Accordingly, until a primer is present on the strand, DNA polymerase will not bind to or copy a nucleic acid strand within the sample. As the presence of a primer controls DNA amplification, the primer may be itself a label. That is, the probe may contain a primer. When the probe finds its match within the sample, a double-stranded nucleic acid having the primer is created. The formation of the double-stranded nucleic acids permits the single-stranded nucleic acid of the sample to be copied. Accordingly, the presence of the double-stranded nucleic acid can be detected by an amplification (i.e. an increase) in the amount of the nucleic acid sequence.

Each of the foregoing techniques relies on probe nucleic acids binding to their complimentary single-stranded nucleic acids within a sample. However, binding to imperfect matches may result. For instance, a probe may match one end of a sequence within the sample, but not the other end. This imperfect match may result in an imperfect double-stranded nucleic acid that resembles a half-zipped zipper. While one end of the probe and sample sequence will form a double strand, the other ends will remain unclosed giving a Y configuration or junction. It is also possible that the ends of a sequence within the sample may match the ends of a probe, but not is middle. In such a situation, double-stranded nucleic acids will be formed at the ends. The middle of such mismatches, however, will bulge rather than form double-stranded nucleic acids. Accordingly, it is possible that the double-stranded nucleotides detected are the result of false positive mismatches. Such false positive mismatches cause it to be believed that certain genes or miRNA are present in the sample, which in fact are not present. These false beliefs regarding the genes or miRNAs present can lead to misdiagnosis and/or selecting an ineffective treatment.

SUMMARY

Exemplary embodiments provide a method for removing a false positive when attempting to detect nucleic acid sequences would provide diagnostics tools with higher fidelity and accuracy. In an effort to remove misleading false positives, GIY-YIG homing endonucleases have been tried. Endonucleases are proteins that destroy nucleic strands. While, GIY-YIG homing endonucleases may cleave a single-stranded 5'-flap of DNA having a Y-shaped junction and a DNA hairpin structure, they exhibit no cleavage activity against RNA. Accordingly, the GIY-YIG homing endonucleases seem incapable of removing false positives from RNA screening and diagnostic methods. Consequently, attempts to diagnose and develop and/or select treatments for diseases involving malfunction and/or hijacking of miRNA protein regulation are limited. These valuable tools may become realized, however, by removing false positive double-stranded nucleic acids comprising one of a bulge and a Y-junction. Such removal may be accomplished by exposing double-stranded nucleic acid sequences comprising a first strand including a single-stranded nucleic acid from the sample to be analyzed and a second strand including a probe to a digestive protein capable of digesting at least one strand of a double-stranded nucleic acid comprising at least one of a bulge and a Y-junction. Such a false positive removing digestive protein may comprise an amino at least 40% identical to amino acid sequence SEQ ID NO: 1. Following this false positive removing digestion, the presence of double-stranded nucleic acids can be detected. In some applications, exposing double-stranded nucleic acids to the digestive protein may digest at least one strand of double-stranded nucleic acids comprising a Y-junction. Digestion by the digestive protein may remove at least one strand of double-stranded nucleic acids comprising a 3' overhang and/or a 5' overhang. Exposure to the digestive protein may remove at least one strand from double-stranded nucleic acids comprising a bulge. Exposure to the digestive protein may remove a nucleic acid strand comprising RNA within the double-stranded nucleic acid. In some applications, a nucleic acid strand comprising DNA within the double-stranded nucleic acid may be removed by exposure to the digestive protein.

Depending on the screening technique utilized, single-stranded nucleotides within the probe and/or sample may be DNA and/or RNA. Accordingly, the false positive double-stranded nucleic acids to be eliminated may comprise DNA and/or RNA. Therefore, effective removal of false positives may be accomplished by a digestive protein having a bifunctional natural with respect to RNA and DNA. Accordingly, the digestive protein may be construct-specific with respect to Y-junctions and bulges. Construct-specific digestion of false positive double-stranded nucleic acids may enable more accurate detection of miRNA, as to provide better diagnosis and/or treatment.

Better diagnosis and/or treatment may be provided by utilizing a digestive protein comprising an endonuclease domain having a bifunctional nature with respect to RNA and DNA and construct-specific activity with respect to 3' overhangs and/or 5' overhangs. Accordingly, the digestive protein may be capable of removing an RNA strand from a false positive double-stranded nucleic acid regardless of the RNA's specific sequence of nucleic acids. Such a digestive protein may include a homing endonuclease derived from *Arabidopsis thaliana*.

Removal of RNA nucleic acid strands from false positive double-stranded nucleic acids may be provided by including within the digestive protein the amino acid sequence SEQ ID NO: 2.

Production of the digestive protein may be made possible with an expression vector comprising a promoter and a nucleic acid sequence encoding an amino acid sequence at least 40% identical to SEQ ID NO:1. Preferably, the amino acid sequence provides a digestive protein functionally equivalent to SEQ ID NO:1, or a portion thereof, such as SEQ ID NO:2.

Producing the digestive protein may done with a host organism carrying an expression vector encoding for the digestive protein. The host organism producing the digestive protein may be a cell or microorganism grown in a culture.

It is to be understood that both the foregoing general description and the following detailed description are exemplary and explanatory, and are intended to provide further explanation of the inventive concepts.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other objects, features and advantages of the inventive concepts will become more apparent to those of ordinary skill in the art by describing in detail exemplary embodiments thereof with reference to the accompanying drawings, in which:

FIG. 10 is an illustration of shortened pri-miR172a.

FIG. 11 shows results analogous of functional equivalence with respect to cleavage of shortened pri-miR172a.

FIG. 12 shows result analogous of functional equivalence with respect to cleavage of a double-stranded nucleic acid region of shortened pri-miR172a.

FIG. 13 shows results analogous of functional equivalence with respect to cleavage of overhangs of the Y-junction of shortened pri-miR172a.

FIG. 14 shows results analogous of functional equivalence with respect to cleavage of overhangs of the Y-junction of shortened pri-miR172a.

FIG. 16 shows results analogous of functional equivalence with respect to cleavage of pre-miR160a.

DETAILED DESCRIPTION OF ILLUSTRATED EMBODIMENTS

Figure 1:
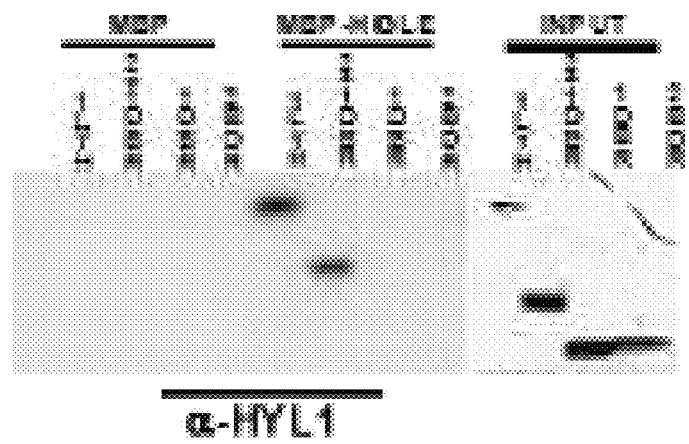
FIG. 1 shows of a pull-down assay analogous of function equivalence with respect to HYL1 binding.

Hereinafter, the inventive concepts will be described with reference to the accompanying drawings. However, the inventive concepts are not limited to the embodiments disclosed below, and can be implemented in various forms. In the drawings, description of parts irrelevant to the detailed description are omitted in order to describe the inventive concepts more clearly, and like numbers refer to like elements throughout the description of the figures.

Unless the context particularly indicates otherwise, it will be further understood that the terms "comprises," "comprising," "includes" and/or "including," when used herein, specify the presence of components and/or elements thereof, but do not preclude the presence or addition of other components and/or elements thereof.

Unless otherwise defined, molecular biology, microbiology, protein purification, protein engineering, and DNA sequencing may be performed using conventional techniques widely used in the recombinant DNA field within the scope of the skill of a person having ordinary skill in the art. The techniques are known to the person having ordinary skill in the art, and disclosed in many standardized textbooks and reference books.

Unless otherwise defined in this specification, all the technical and scientific terms used herein have the same meanings as what are generally understood by a person skilled in the related art to which the inventive concepts belong.

Various science dictionaries including the terms included in this specification are widely known and used in the related art. Although any method and material similar or equivalent to those disclosed in this specification are found to be used to put the inventive concepts into practice or used for experiments, several methods and materials are disclosed in this specification. Since certain methodologies, protocols and reagents may be widely used depending on the contents used by those skilled in the art, the methodologies, protocols and reagents are not intended to limit the scope of the inventive concepts.

As used in this specification, the singular forms "a," "an" and "the" are intended to include the plural forms as well, unless the context clearly indicates otherwise. Also, a nucleic acid sequence is written in this specification, including sequence listings, in a left-to-right direction, that is, a 5' to 3' direction, and an amino acid sequence is written in this specification, including sequence listings, in a left-to-right direction, that is, an amino-to-carboxyl direction, unless the context clearly indicates otherwise.

Hereinafter, the inventive concepts will be described in further detail.

Eliminating at least a portion of false positives when detecting a nucleic acid may be accomplished by creating a plurality of double-stranded nucleic acids by hybridizing a plurality of single-stranded nucleic acids within a sample with a plurality of probe nucleic acids. Created via complimentary base pairing, the double-stranded nucleic acids comprise a first strand including at least one of the single-stranded nucleic acids of within a sample, and a second strand including at least one of the plurality of probes. False positives may then be removed by exposing the double-stranded nucleic acids to a digestive protein comprising capable of digesting at least one of the first strand and the second strand of a double-stranded nucleic acid comprising at least one of a bulge and a Y-junction. Following exposure to the digestive protein, the presence of double-stranded nucleic acids may be detected. Binding of the digestive protein to double-stranded nucleic acids may be enhanced by including within the digestive protein a DNA binding domain. Accordingly, the digestive protein may comprise a DNA binding domain. A flexible linker connecting the DNA binding domain to an endonuclease domain may be also present within the digestive protein. The endonuclease domain of the digestive protein may have a bifunctional nature as to be capable of digesting RNA and DNA nucleic acid strands.

As to permit removal of false positive double-stranded nucleic acids while they are being created, the digestive protein may have construct-specificity with respect to Y-junctions and/or bulges. The digestive protein may have construct specificity with respect to 3' overhangs and 5' overhangs. Either construct specificity may limit the digestion of single-stranded nucleic acids. Only digesting a small amount, if any, of the single-stranded nucleic acids, a construct-specific digestive protein would not unduly inhibit the formation of double-stranded nucleic acids. Nor would such a digestive protein remove true positive double-stranded nucleic acids. Rather, digestion would be limited to false positive double-stranded nucleic acids. A digestive protein having such construct-specificity may include a homing endonuclease, such as HYL1 interacting GIY-YIG-like endonuclease (HIGLE). Although HIGLE is not related to any RNase type III family involved in the metabolism of sRNA, HIGLE may remove 5' and 3' overhangs to process pri-miRNA into a pre-miRNA-type intermediate. Some forms of HIGLE may have a bifunctional nature based on RNA and DNA. A construct specific bifunctional nature may be provided by incorporating HIGLE into the digestive protein. Unlike conventional GIY-YIG homing endonucleases, HIGLE has sequence-non-specific activity and may act as an RNA endonuclease. Having RNA endonuclease activity, the incorporation of HIGLE into the digestive protein may element false positives when attempting to detect miRNA for diagnostic and/or other purposes. Accordingly, false positive double-stranded nucleic acids comprising at least one of a bulge and a Y-junction may be removed by incorporating HIGLE and/or other RNA endonucleases within the digestive protein.

The term "endonuclease" refers to an enzyme that hydrolyzes a phosphodiester bond in a nucleic acid backbone. Accordingly, an "endonuclease" is an enzyme that breaks the bonds holding individual nucleic acids together within a nucleic acid strand. Breaking the bonds holding nucleic acids strands together, a protein having endonuclease activity may be capable of digesting a nucleic acid strand.

Proteins having endonuclease activity are believed to be involved in the production and/or maturation of miRNA. In plants, for instance, a microprocessor for the production and/or maturation miRNA may be generally composed of dicer-like protein 1 (DCL1), hyponastic leaf 1 (HYL1), and serrate (SE). Such a microprocessor protein may interact with at least 7 proteins during miRNA maturation process.

The digestive protein may comprise a homing endonuclease. Homing endonucleases belong to a family of endonucleases that catalyze a gene conversion phenomenon in which an endonuclease-coding allele of a certain gene propagates into an endonuclease-deficient allele. At least five types of the homing endonuclease are known, including i) a LAGLIDADG homing endonuclease, ii) a HNH homing endonuclease, iii) a His-Cys box homing endonuclease, iv) a GIY-YIG homing endonuclease, and v) a cyanobacterial homing endonuclease.

The digestive protein may include a GIY-YIG endonuclease domain, which is commonly found in some homing endonucleases.

The digestive protein may include an α/β structure. A possible α/β structure the digestive protein may adopt may comprise a three-stranded antiparallel β-sheet structure. The flat β-sheet may be flanked by three α-helixes. Accordingly, the digestive protein may include a flat portion flanked by three protein coils. This or other α/β structures may provide the digestive protein with a nucleic acid binding domain. As to permit the removal of false positive double-stranded nucleic acids, the digestive protein preferably comprises an endonuclease domain. The endonuclease domain of the digestive protein may comprise a sequence of approximately 90 to 100 amino acids. In some embodiments, the endonuclease domain may comprise a GIY-YIG motif including a space spanning region between the -GIY- sequence and a -YIG- sequence. In some embodiments, the space spanning region may comprise approximately 10 to 11 amino acids. It should be noted that the name YIG-sequence and GIY-sequence do not indicate sequences comprising only glycine (G), isoleucine (I) and tyrosine (Y). Rather, the GIY or YIG sequence may comprise other amino acid residues such as leucine (L) and/or valine (V). Accordingly, the GIY-sequence and/or the YIG-sequence may comprise YLL, YVG and other variants. The digestive protein may, therefore, comprise an endonuclease domain including an amino sequence functionally equivalent to SEQ ID NO: 2, which contains a YLL variant of the GIY sequence.

Functional equivalence to SEQ ID NO: 2 may be provided by including a glycine residue within the space spanning of the GIY-YIG motif. Incorporating approximately 8 to 10 arginine residues downstream from the -GIY-sequence may provide an endonuclease domain functionally equivalent to endonuclease domain. A sequence functionally equivalent to SEQ ID NO: 2 may comprise a negatively charged, metal-binding amino acid residue, such as glutamic acid, at approximately 30 residues downstream of the GIY-YIG motif and an polar, uncharged residue, such as asparagine, upstream of the negatively charged, metal-binding amino acid residue.

The digestive protein may comprise a portion belonging to the SLX1 cluster of the family of highly diverse GIY-YIG endonucleases.

In some embodiments, the endonuclease domain of the digestive protein may cleave a single-stranded 5'-flap of a Y-junction and/or a bulge. The endonuclease domain of the digestive protein may exhibit construct-specific cleavage activity with respect to 3' overhangs and/or 5' overhangs of Y-junctions. A bifunctional nature with respect to RNA and DNA may be present in the digestive protein.

An imperfect match between a probe nucleic acid and a single-stranded nucleic acid within the sample may result in a false positive double-stranded nucleic acid sequence. For instance, a probe may match one end of a sequence within the sample, but not the other end. This imperfect match may result in an imperfect double-stranded nucleic acid comprising a Y-junction. It is also possible that the ends of a single-stranded nucleic acid within the sample may match the ends of a probe nucleic acid strand, but not is middle. In such a situation, double-stranded nucleic acids will be formed at the ends. The middle of such a false positive double-stranded nucleic acid, however, may comprise a bulge.

Incorporating into the digestive protein HIGLE or otherwise providing an endonuclease domain functionally equivalent to SEQ ID NO: 2 may remove at least a portion of the false positive double-stranded nucleic acids by digesting at least one stand of the double strands in a sequence non-specific, construct specific manner.

Construct specific, sequence non-specific digestion of at least one strand within a false positive double-stranded nucleic acid may be provided by including a within the digestive protein a sequence at least 40% identical to amino acid sequence SEQ ID NO: 1 as a result of addition, substitution or deletion of amino acids. Preferably, the functional equivalence of SEQ ID NO: 2 contained with SEQ ID NO: 1 is persevered. Preserving such functional equivalence may be accomplished by maintaining an endonuclease domain of approximately 90 to 100 amino acids in length. Maintaining a GIY-YIG motif may also preserve functional equivalence in some embodiments. Preferably, the maintained GIY-YIG motif comprises a GIY-sequence, a YIG-sequence and a space spanning region between the GIY-sequence and the YIG-sequence comprising glycine. A space spanning region of approximately 10 to 11 amino acids in length may preserve functional equivalence. Functional equivalence may also be maintained by incorporating 8 to 10 arginine residues downstream of the GIY-sequence. The digestive protein may maintain functional equivalence by comprising a negatively charged metal binding amino acid residue, such as glutamic acid, approximately 30 residues downstream of the GIY-YIG motif, and a polar uncharged amino acid residue, such as asparagine, upstream of the negatively charged, metal binding amino acid residue. Preserving functional equivalence in may be accomplished by including a positively charged amino acid residue, such as arginine, approximately 6 residues downstream of the GIY-YIG motif. Functional equivalence may be preserved by a negatively charged amino acid residue, such as glutamic acid, approximately 56 residues downstream of the GIY-YIG motif. When functional equivalence is preserved, the digestive protein should digest at least one strand of a false positive double-stranded nucleic acid. Preserving such functional equivalence permits false positive double-stranded nucleic acids comprising a Y-junction and/or bulge to be removed. Preferably, the sequence non-specific digestive activity is preserved in the digestive protein. A digestive protein having preserved functional equivalence will be capable of digesting RNA nucleic strands and/or DNA nucleic acid strands within false positive double-stranded nucleic acids. Accordingly, the digestive protein may comprise an amino acid sequence SEQ ID NO: 1, which includes as the endonuclease domain SEQ ID NO: 2.

With regards to preserving functional equivalence, the digestive protein should comprise an amino acid sequence at least 40% or more, preferably 80% or more, more preferably 90% or more, and most preferably 95% or more homologous with respect to the amino acid sequence of SEQ ID NO: 1 as a result of addition, substitution or deletion of amino acids. The sequence homology may be determined by comparing two optimally aligned sequences, and a portion of the amino acid sequence in the comparison region may be added or deleted.

The digestive protein may comprise an amino acid sequence completely matching a 368 amino acid sequence of a protein encoded by the locus At2g30350.

The digestive protein may comprise an endonuclease domain belonging to the SLX1 cluster in the family of GIY-YIG endonucleases, as assessed through BLAST analysis. The digestive protein may lack a circular DNA-binding domain and a domain homologous to the SLXI GIY-YIG domain. The digestive protein may comprise a domain 46 to 83% identical to SLX1 GIY-YIG domains. A domain 83% identical to the unidentified GIY-YIG domains from maize and/or may be included the digestive protein.

The digestive protein may comprise a domain 54% identical to the SLX1 protein from a human and/or 46% identical to the SLX1 protein from yeast.

The digestive protein may be provided by transfecting a host organism with an expression vector comprising a nucleic acid sequence encoding at least the endonuclease of the digestive protein. In some embodiments, the endonuclease encoded permits false positive double-stranded nucleic acids comprising a Y-junction and/or bulge to be removed. Preferably, the encoded endonuclease has sequence non-specific digestive activity. In some embodiments, the encoded endonuclease may be capable of digesting RNA nucleic strands and/or DNA nucleic acid strands within double-stranded nucleic acids. Accordingly in some embodiments, the encoded endonuclease may comprise an amino acid sequence SEQ ID NO: 1, which includes SEQ ID NO: 2. In some embodiments, the encoded endonuclease may comprise an amino acid sequence at least 40% or more, preferably 80% or more, more preferably 90% or more, and most preferably 95% or more homologous with respect to the amino acid sequence of SEQ ID NO: 1 as a result of addition, substitution or deletion of amino acids.

The expression vector may comprise a bacterium, a plasmid, a phage, a cosmid, an episome, a virus and/or an insertable DNA fragment (i.e., a fragment insertable into the host cell genome by means of homologous recombination). Embodiments of the expression vector including a plasmid may comprise a circular double-stranded DNA loop. In some embodiments, the expression vector may comprise a plasmid capable of ligating an additional DNA to an inner part thereof. In some embodiments, the expression vector may comprise a viral vector capable of ligating additional DNA into a viral genome.

In some embodiments, the expression vector may comprise at least one pET-3a-d, pET-9a-d, pET-11a-d, pET-12a-c, pET-14b, pET-15b, pET-16b, pET-17b, pET-17xb, pET-19b, pET-20b(+), pET-21a-d(+), pET-22b(+), pET-23a-d(+), pET-24a-d(+), pET-25b(+), pET-26b(+), pET-27b(+), pET-28a-c(+), pET-29a-c(+), pET-30a-c(+), pET-30 Ek/LIC, pET-30 Xa/LIC, pET-31b(+), pET-32a-c(+), pET-32 Ek/LIC, pET-32 Xa/LIC, pET-33b(+), pET-34b(+), pET-35b(+), pET-36b(+), pET-37b(+), pET-38b(+), pET-39b(+), pET-40b(+), pET-41a-c(+), pET-41 Ek/LIC, pET-42a-c(+), pET-43.1a-c(+), pET-43.1 Ek/LIC, pET-44a-c(+), pRSETA, pRSETB, pRSETC, pESC-HIS, pESC-LEU, pESC-TRP, pESC-URA, Gateway pYES-DEST52, pAO815, pGAPZ A, pGAPZ B, pGAPZ C, pGAPα A, pGAPα B, pGAPα C, pPIC3.5K, pPIC6 A, pPIC6 B, pPIC6 C, pPIC6α A, pPIC6α B, pPIC6α C, pPIC9K, pYC2/CT, pYD1 Yeast Display Vector, pYES2, pYES2/CT, pYES2/NT A, pYES2/NT B, pYES2/NT C, pYES2/CT, pYES2.1, pYES-DEST52, pTEF1/Zeo, pFLD1, PichiaPink™, p427-TEF, p417-CYC, pGAL-MF, p427-TEF, p417-CYC, PTEF-MF, pBY011, pSGP47, pSGP46, pSGP36, pSGP40, ZM552, pAG303GAL-ccdB, pAG414GAL-ccdB, pAS404, pBridge, pGAD-GH, pGAD T7, pGBK T7, pHIS-2, pOBD2, pRS408, pRS410, pRS418, pRS420, pRS428, yeast micron A form, pRS403, pRS404, pRS405, pRS406, pYJ403, pYJ404, pYJ405, and pYJ406.

Transfecting a host organism with the expression vector preferably provides the host organism the ability to manufacture the digestive protein. Accordingly, the expression vector may comprise a promoter. Preferably the promoter is recognized by the host organism.

The promoter may comprise at least one of SBE4, 3TP, PAI-1, p15, p21, CAGA12, hINS, A3, NFAT, NFKB, AP1, IFNG, IL4, IL17A, IL10, GPD, TEF, ADH, CYC, INU1, PGK1, PHO5, TRP1, GAL1, GAL10, GUT2, tac, T7, T5, nmt, fbp1, AOX1, AOX2, MOX1, and FMD1 promoters.

Preferably the promoter sequence is operably linked to the nucleic acid sequence encoding the digestive protein such that the promoter is capable of inducing expression of the digestive protein by the host organism.

A regulatory sequence may be including in the expression vector. The regulatory sequence may comprise at least one of Shine-Dalgano sequence of a replicase gene in phage MS-2, and a Shine-Dalgano sequence of bacteriophage lambda (λ) cII. Different regulatory sequences may be included within the expression vector.

As to permit identification of transfected organisms, the expression vector may comprise a marker gene. Identification of transfected organisms with the marker gene may be based on the ability of the organism to survive and/or thrive in otherwise adverse environments. For example, transfected bacteria may be identified based on their ability to survive and/or thrive in mediums containing an antibiotic. Accordingly, the marker gene may comprise an antibiotic-resistant gene. The antibiotic resistant gene may comprise at least one of a hygromycin-resistant gene, a kanamycin-resistant gene, a chloramphenicol-resistant gene, and a tetracycline-resistant gene. Identification of transfected organism may also be accomplished based on the emission of light from the transfect organisms. Accordingly, the marker gene may comprise a fluorescent protein gene. When such marker genes are utilized, transfected organisms may be identified based on their ability to emit light. The fluorescent protein gene may comprise at least one of a yeast-enhanced green fluorescent protein (yEGFP) gene, a green fluorescent protein (GFP) gene, a blue fluorescent protein (BFP) gene, and a red fluorescent protein (RFP).

Preferably, the host organism is capable of being transformed by genetic engineering to effectively express a gene.

The host organism may be a cell. Accordingly, the host organism may be at least one of a microorganism, an animal cell, a plant cell, a culture cell derived from an animal, and a culture cell derived from a plant. The cell may be at least one of a wild-type cell and a modified cell.

Transfected host cells may be cultured under batch, fed-batch and/or continuous fermentation conditions.

Effective conventional batch fermentation may utilize at least one of a closed system comprising preparing a culture medium, inoculating the culture medium with the host organism, and fermenting the culture medium inoculated with the host organism. Fermentation may occur without adding any additional components to the medium. Fermentation may include varying at least one of pH, oxygen content, and carbon source. The metabolites and cellular biomass present may constantly vary during fermentation stops. The host organism may progress throughout a high-growth log phase on a stationary member. Growth of the host organism may reach a stationary phase during which the growth rate is reduced and/or growth is stopped. The most digestive protein may be produced during the log phase.

Nutrients may be added when the concentration of host organisms drops below a threshold value. The added nutrients may comprise at least one of a carbon source, a nitrogen source, and $O_2$. Adding nutrients in response to declining amounts of the host organism may be useful when catabolite repression inhibits cell metabolism and/or it is desirable that the medium include a limited amount of nutrients. The concentration of nutrients present may be predicted based on a change in a measurable factor, such as pH, dissolved oxygen, and/or partial pressure of $CO_2$ and/or other waste gases. Fermentation may comprise continuously adding a defined culture medium and extracting the same amount of medium. Such fermentation may permit sustaining a constant high-density culture following log phase growth of the host organism. Fermentation may comprise manipulating one or more factors effecting growth of the host of organism and/or a concentration of the digestive protein.

Fermentation may comprise continuously varying a factor having a great influence on growth, while maintaining the host organism at a constant concentration. The concentration of host organism may be measured by the medium turbidity.

The digestive protein may be functionally equivalent to SEQ NO: 1 with regards to the ability to form a protein complex with HYL1. Such functional equivalence may be assessed via a pull-down assay performed in vitro.

The pull-down assay may be conducted using a variant of the digestive protein, or a portion thereof, in which the N-terminus and the C-terminus have been deleted. The variant of the digestive protein can be expressed as a protein fused with a maltose-binding protein (MBP). The three sites of the N-terminus and the C-terminus can be HA-tagged. This fused protein can be purified by MBP-affinity chromatography.

Similarly, HYL1 and a deletion variant including RNA-binding domain 1 and RNA-binding domain 2 at the N-terminus can be expressed, and purified using histone-affinity chromatography. A pull-down assay demonstrating functional equivalence to SEQ ID NO: 1 with regards to the ability to form a protein complex with HYL1 may resemble that shown in FIG. 1, wherein HIGLE denotes a sequence functionally equivalent to SEQ ID NO: 1.

Functional equivalence to SEQ ID NO: 1 may be demonstrated using an MBP-fused digestive protein-HA protein variant mixed with HIS-fused HYL1 and a deletion variant protein subjected to pull-down analysis in an amylose resin.

Figure 2:
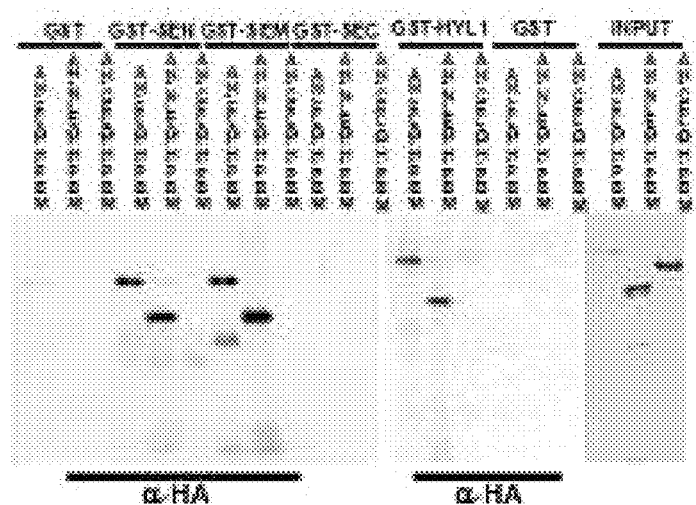
FIG. 2 show results analogous of function equivalence with respect to HYL1 binding.

A digestive protein functionally equivalent to SEQ ID NO: 1 with respect to HYL1 binding should be capable of providing a MBP-digestive protein-3HA capable of pulling down HYL1 and RBD1+2 domains, without pulling down the separate RNA-binding domain down. Such functional equivalence should provide results analogous to those shown in FIG. 2, with HIGLE representing the protein functionally equivalent to SEQ ID NO: 1. In such an analysis, the MBP protein can be used as a negative control, and should not allow either HYL1 or a deletion variant to be recovered, as also shown in FIG. 2.

Functional equivalence to SEQ ID NO: 1 with respect to the ability to form a protein complex with HYL1 can be assessed by performing co-immunoprecipitation analysis between the digestive, HYL1 and SE. In such an analysis, GST-fused HYL1 can be used to determine interaction with the digestive protein. A digestive protein functionally equivalent to SEQ ID NO: 1 may include a region permitting GST-HYL1 binding as to provide co-immunoprecipitation similar to that shown in FIG. 3. A co-immunoprecipitation analysis may also utilize a GST-fused SE-deletion variant. Both N-terminal and middle regions of SE may interact with a digestive protein functionally equivalent to SEQ ID NO: 1, with respect to binding. Accordingly, the results of an analysis demonstrating binding functional equivalence may resemble those shown in FIG. 2.

Figure 3:
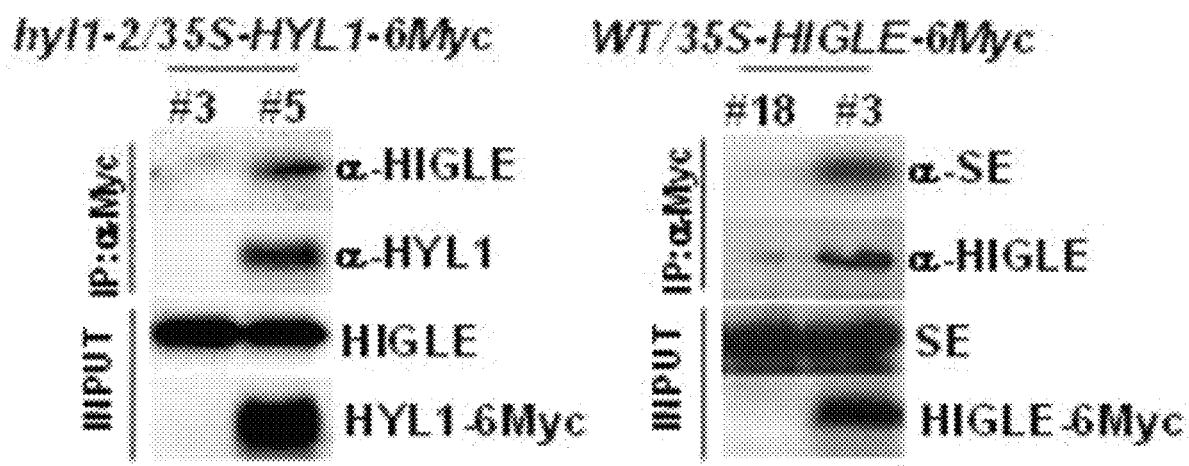
FIG. 3 shows results of a co-immunoprecipitation analysis analogous of functional equivalence with respect to binding to HYL1 and SE.

The digestive protein may be functionally equivalent to SEQ ID NO: 1 with respect to the ability to bind to the N-terminus of HYL1, the N-terminal region of SE and/or the middle region of SE. Such functional equivalence may be evaluated utilizing a co-immunoprecipitation method performed on a WT/35S-digestive protein-6Myc and/or hyl1-2/35S-HYL1-6Myc gene-transplanted plant. The precipitation of MYC can be verified using an anti-MYC antibody. The precipitation of the digestive protein, HYL1 and/or SE can be verified using anti-digestive protein, anti-HYL1, and/or anti-SE antibodies. Binding specificity of the antibodies may be checked by using a knocked-down transgenic plant as a negative control. Functional equivalence of the digestive protein with respect to HYL1 binding should permit HYL1-6myc to co-immunoprecipitate with the digestive protein. Likewise, functional equivalence with respect to SE binding should permit digestive protein-6Myc to c-immunoprecipitate with α-Myc antibody, as to provide detectable endogenous SE in the precipitation complex. Such co-immunoprecipitation should produce results analogous to those shown in FIG. 3, with the digestive protein taking the place of HIGLE. In FIG. 3, hyl1-2/35S-HYL1-6Myc line 3 and WT/35S-HIGLE-6Myc line 13 correspond to negative controls.

The digestive protein may be functionally equivalent to SEQ ID NO: 1 with respect to nuclear localization. Such functional equivalence may be provided by nuclear localization signals at the N-terminal and C-terminal regions of the digestive protein. Functionally equivalent nuclear localization may be assessed using WT/35S-digestive protein-fluorescent protein. Presence of fluorescence within the nucleus would be indicative of equivalent nuclear localization.

Figure 4:
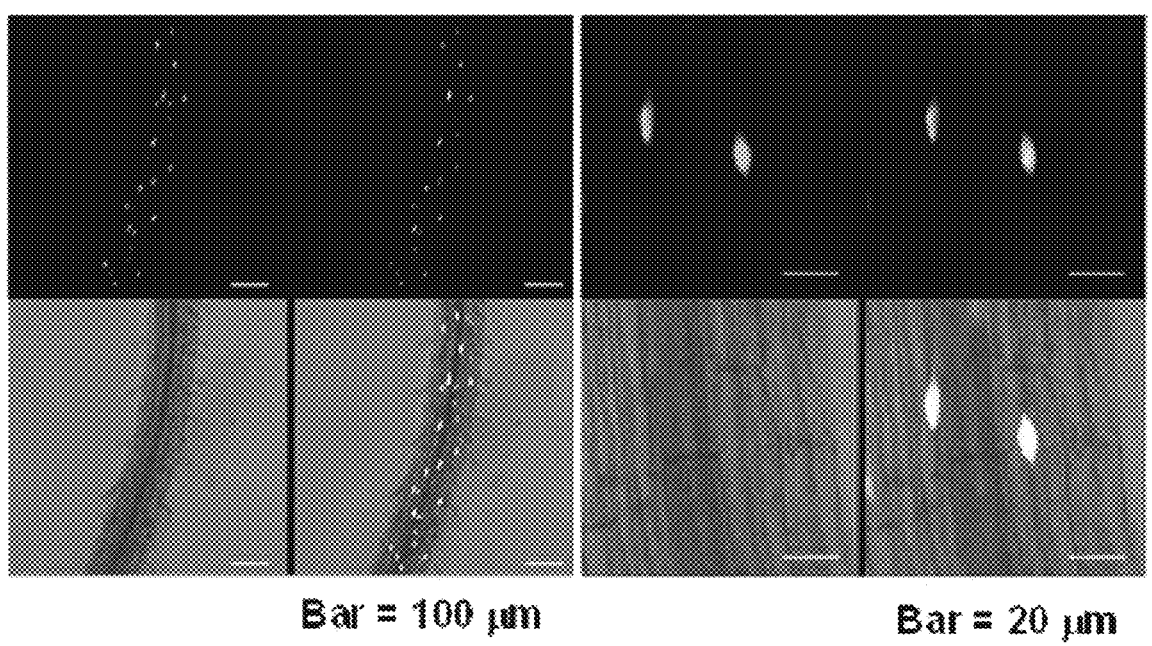
FIG. 4 shows fluorescent signal analogous of functional equivalence with respect to localization within the nucleus of a cell.

The digestive protein may be functionally equivalent to SEQ ID NO: 1 with respect to nuclear co-localization with HYL1. Such functional equivalence may be assessed using a double transgenic plant line WT/35S-HYL1-CFP/35S-digestive protein-YFP. Use of YFP fluorescent protein should provide the digestive protein construct with a yellow light. Accordingly, the ability of the digestive protein to localize in the nucleus should be demonstrated by the presence of a yellow light within the nucleus, as shown in FIG. 4, with HIGLE taking the place of the digestive protein. The CFP fluorescent protein should provide HYL1 a blue light. Accordingly, the co-occurrence of a blue light and a yellow light within the nuclease, as also show in FIG. 4, indicates the ability of the digestive protein to co-localize with HYL1 in the nucleus.

Figure 5:
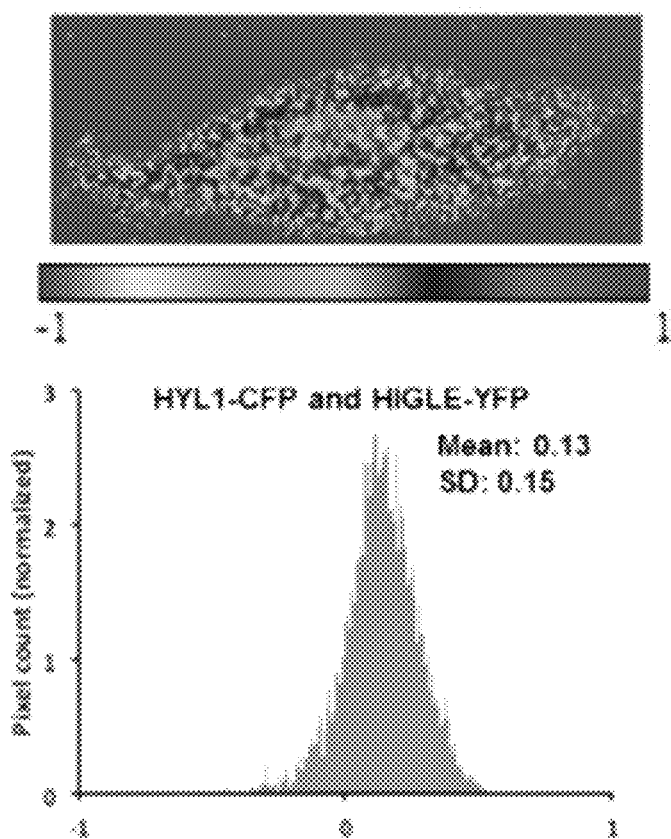
FIG. 5 shows a FRET analysis analogous of functional equivalence with respect to proximity to HYL1 when localized to the nucleus of a cell.

The digestive protein may be functional equivalent to SEQ ID NO: 1 with regards to the proximity to HYL1 when localized to the nucleus. The ability of a digestive protein to have equivalent proximity to HYL1 within the nucleus can be evaluated using fluorescence resonance energy transfer (FRET) analysis. The FRET analysis may be performed using CFP fused HYl1 and a YFP fused digestive protein. Such a functionally equivalent digestive protein may provide results analogous to those shown in FIG. 5. Accordingly, functional equivalence with respect to proximity to HYL1 may be demonstrated by an energy transfer indicating a distance of less than 100 Å.

Figure 6:
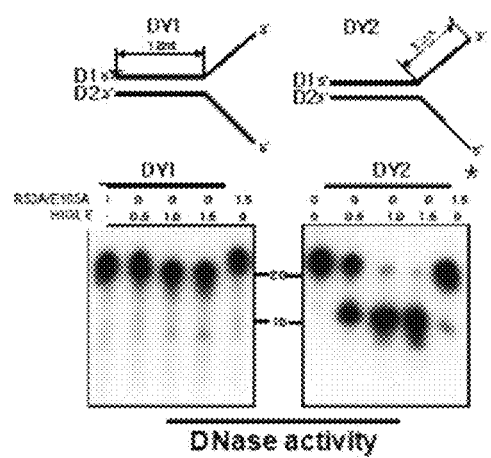
FIG. 6 shows results analogous of functional equivalent with respect to removal of double-stranded DNA comprising a Y-junction.

The digestive protein may be functionally equivalent to SEQ ID NO: 1 with regards to the ability to remove a nucleic strand from a double-stranded DNA having at least one of a bulge and a Y-junction. Such functional equivalence may be evaluated by performing a processing analysis using double-stranded DNA having a Y-junction as a substrate. The double-stranded DNA may be analogous to that shown in FIG. 6, comprising two double-stranded DNAs having identical nucleotide sequence. Ideally the double strands differ only in that one is labeled in an overhang of the Y-junction whereas the other is labeled in the double-stranded portion. A radioactive phosphate may be used to label the strands. Functional equivalence with respect to the ability to remove double strands comprising a Y-junction should provide results analogous to those shown in FIG. 6, in that digestion of the overhang should occur faster than digestion of the double-stranded portion.

Figure 7:
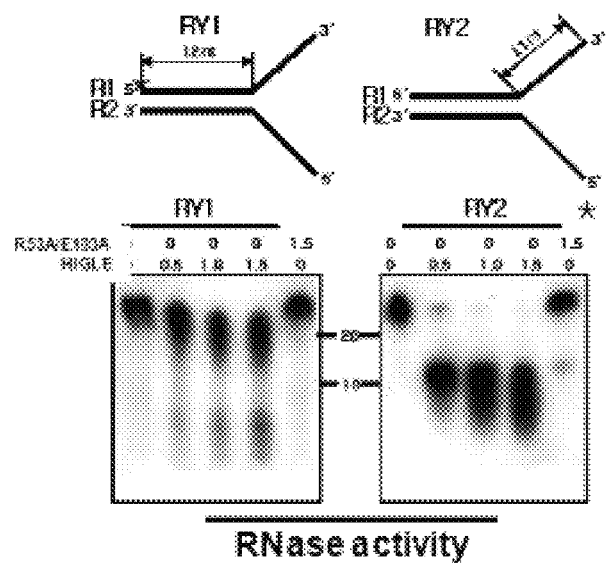
FIG. 7 shows results analogous of functional equivalent with respect to removal of double-stranded RNA comprising a Y-junction.

The digestive protein may be functional equivalent with the respect to SEQ ID NO: 1 with regards to the ability to remove a nucleic strand from a double-stranded RNA having at least one of a bulge and a Y-junction. Such functional equivalence may be evaluated by performing a processing analysis using double-stranded RNA having a Y-junction as a substrate. The double-stranded RNA may be analogous to that shown in FIG. 7, comprising two double-stranded RNAs having identical nucleotide sequences. Ideally the double strands differ only in that one is labeled in an overhang of the Y-junction whereas the other is labeled in the double-stranded portion. A radioactive phosphate may be used to label the strands. Functional equivalence with respect to the ability to remove double strands comprising a Y-junction should provide results analogous to those shown in FIG. 7, in that digestion of the overhang should occur faster than digestion of the double-stranded portion.

The digestive protein may be functionally equivalent to SEQ ID NO: 1 with regards to the ability to remove RNA nucleic strands and DNA nucleic strands from a double-stranded nucleic acid comprising at least one of a Y-junction and a bulge. Such functional equivalence may provide results analogous to those presented in both FIGS. 6 and 7.

Figure 8:
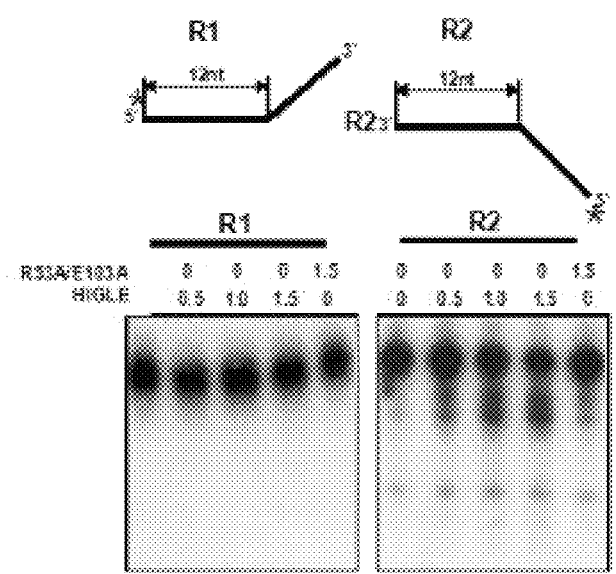
FIG. 8 shows results analogous of functional equivalence with respect to construct specificity towards double-stranded nucleic acids.

The digestive protein may be functionally equivalent to SEQ ID NO: 1 with regards to construct-specificity. Such functional equivalence can be determined by performing a processing analysis using singled stranded RNA. Functional equivalence with respect to construct specificity towards double-stranded nucleic acids may provide results analogous to those shown in FIG. 8, in that digestion of the single-stranded nucleic acids is limited.

Figure 9:
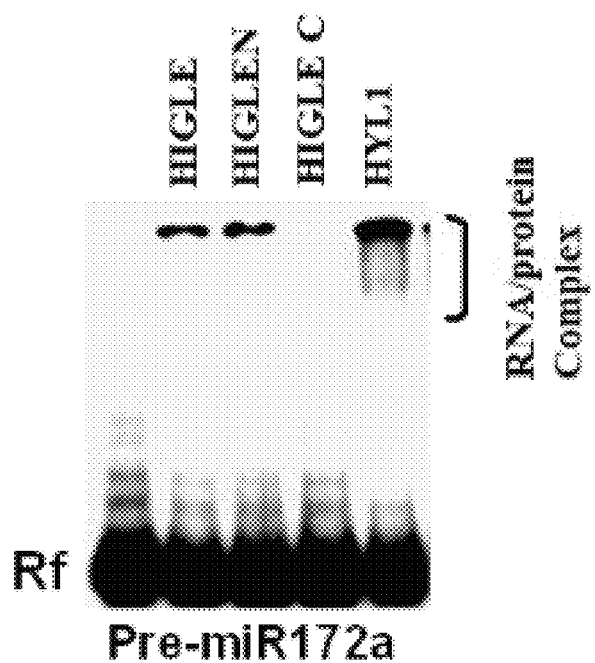
FIG. 9 shows results analogous of functional equivalence with respect to the ability to bind pre-miR172.

The digestive protein may be functionally equivalent to SEQ ID NO: 1 with regards to the ability to bind to pre-miR172a, a precursor of the miRNA miR172. Such functional equivalence can be assessed using a gel shift assay (EMSA) utilizing pre-miR172a as a substrate. The presence of such functional equivalence may provide results analogous to those shown in FIG. 9, with HIGLE representing the protein functionally equivalent to SEQ ID NO: 1.

The digestive protein may be functionally equivalent to SEQ ID NO: 1 with respect to biding affinity to pre-miR172a. A dissociation constant of approximately $1.5 \pm 0.7 \times 10^{-7}$ may be indicative such functional equivalence. Such functional equivalence may be provided by including within the endonuclease domain of the digestive protein a positively charged amino acid residue, such as arginine, approximately 6 residues downstream of the GIY-YIG motif and/or a negatively charged amino acid residue, such as glutamic acid, approximately 56 residues downstream of the GIY-YIG motif.

Figure 10:
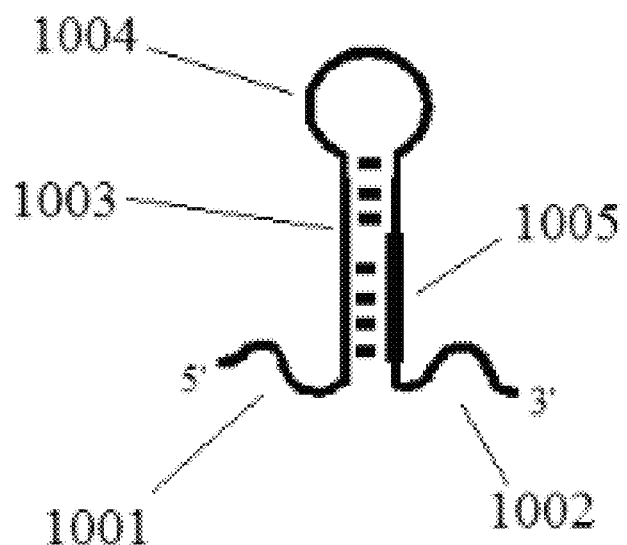

Given the difficulty in handling pri-miR172a under experimental due to its length, functional equivalence with regards to binding and affinity to pri-miR172a may be assessed using a pri-miR172a substrate including deleted 5' and 3' overhangs. As depicted in FIG. 10, such a shorten pri-miR172a substrate may comprise a 5'-single-stranded overhang 1001 of approximately 85 nucleotides in length, 3'-single-stranded overhang 1002 of approximately 78 nucleotides in length, a double-stranded nucleic acid sequence 1003 of approximately 102 in length, a bulge 1004, and pri-miR172 1005.

Figure 11:
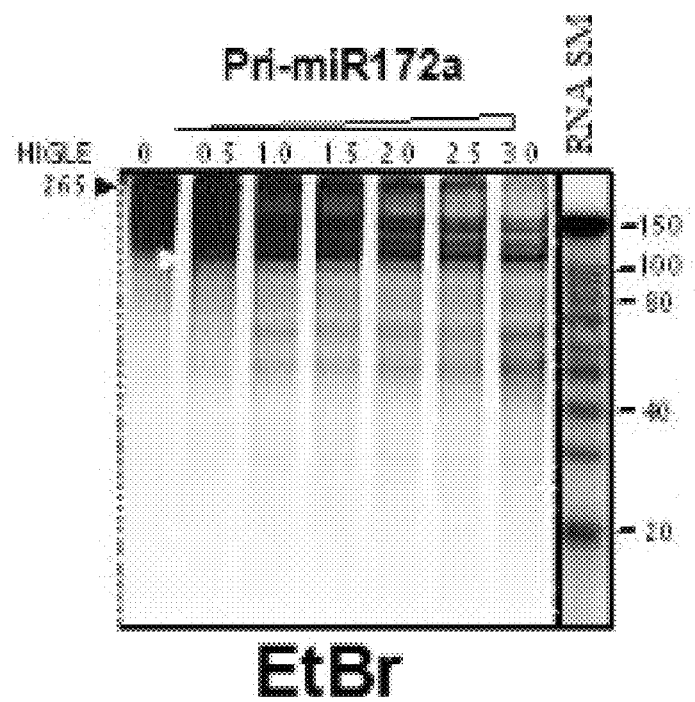

The digestive protein may be functionally equivalent to SEQ ID NO: 1 with respect to cleavage of the shortened pri-miR172a substrate. Such functional equivalence may be determined by culturing the shortened pri-miR172a substrate with an increasing concentration (0 to $3.0 \times 10^{-8}$ g) of digestive protein and then separating the resulting fragments based on size. Functional equivalence with respect to cleavage of the shortened substrate should provide results analogous to those presented in FIG. 11, with HIGLE representing the digestive protein. That is the functionally equivalent digestive protein should cleave the shortened pri-miR172a into fragments having sizes ranging from 50 to 150 nucleotides.

The digestive protein may be functionally equivalent to SEQ ID NO: 1 with respect to the pattern of cleavage of the shortened pri-miR172a substrate. Such functional equivalence can be determined by performing RNA blot analysis using probes specific for at least one of the 5'-single-stranded overhang 1001, the 3'-single-stranded overhang 1002, the bulge 1004 and pri-miR172 1005. Blotting with the probe for the pri-miR172 1005 should provide results analogous to those shown in FIG. 12. That is pri-miR172 1005 of the double-stranded nucleic acid sequence 1003 should not be cut. With respect to the results shown in FIG. 12, HIGLE represent the digestive protein. Failure of the digestive protein to cut, cleave or otherwise digest pri-miR172 is demonstrated by the present presence of the pri-miR172 signal from the probe for primiR172 1005, despite increasing concentrations of the digestive protein (in this case HIGHLE). The approximately 100 nucleotide-long and approximately 60 nucleotide-long fragments may be a pre-miR172a-type intermediate, and a further truncated derivative. These results may be verified by sequencing the resulting fragments to verify that the fragments are the double-stranded nucleic acid sequence 1003 of pre-niR172a. Sequencing of the fragments obtained from the analysis of FIG. 12 verifies that the fragments are actually the double-stranded nucleic acid sequence 1005 of pri-miR172a.

Figure 12:
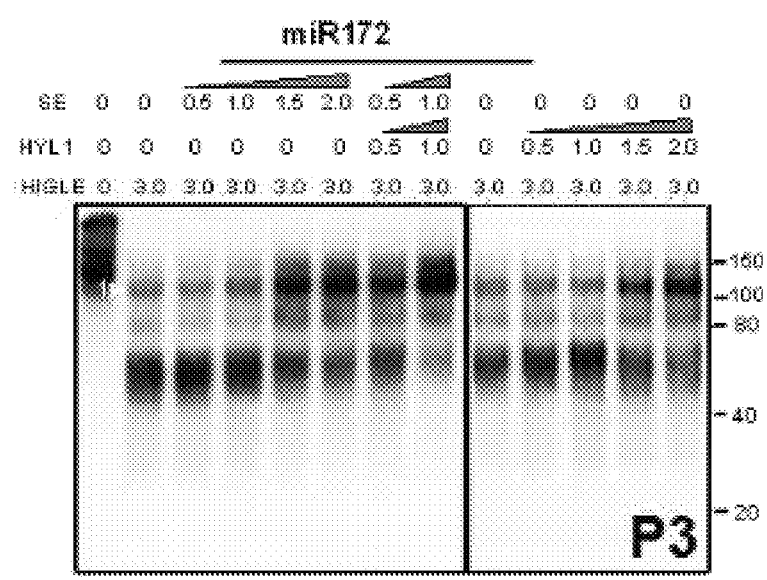

Also shown in FIG. 12 is a further analysis that can demonstrate functional equivalence with respect to potentiation of SE and/or HYL1 on digestion of double-stranded nucleic acids comprising at least one of a Y-junction and a bulge. Such functional equivalence can be evaluated by maintaining the digestive protein, represented by HIGLE, at a constant concentration of approximately $3.0 \times 10^{-8}$ g and increasing the concentration of HYL1 and/or SE. As shown in FIG. 12, increasing amounts of the SE or HYL1 should cause increased production of the approximately 100 nucleotide-long fragment. Conversely, decreased production the approximately 60 nucleotide-long fragment should result from increased amounts of SE and HYL1. The approximately 100 nucleotide-long intermediate fragment may be more effectively accumulated by SE (4 fold), compared to that of HYL1 (2 fold). Furthermore, the production increasing effects of HYL1 and SE on the digestive protein may be additive, with the presence of both increasing production of the 100 nucleotide-long fragment approximately 6 fold.

Figure 13:
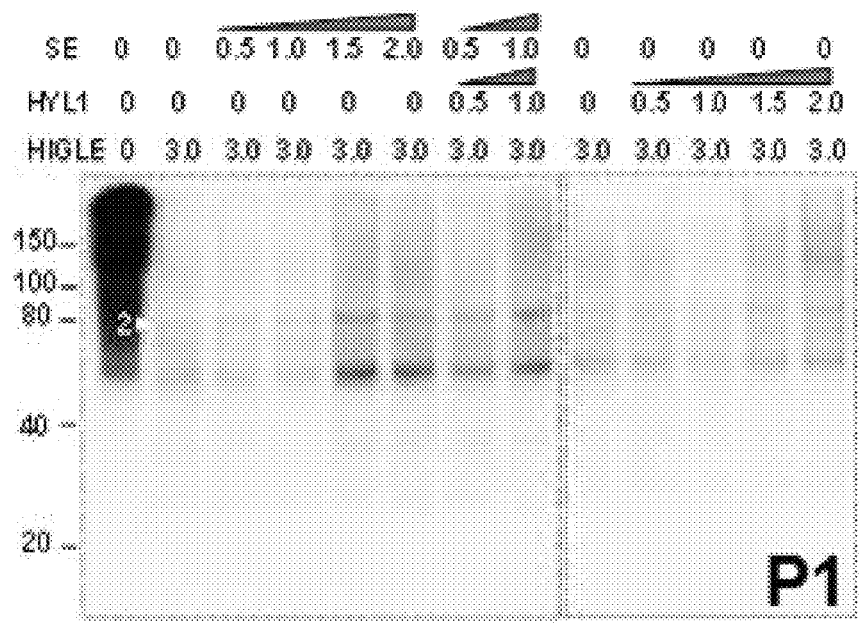
Figure 14:
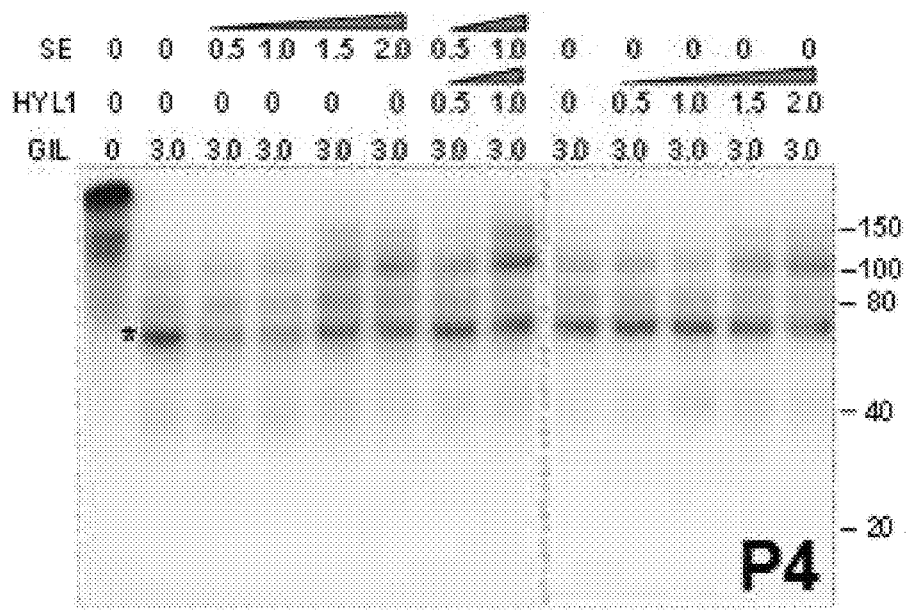

The digestive protein may be functional equivalent to SEQ ID NO: 1 with respect to cleavage of at least one of the 5'-single-stranded overhang 1001 and/or the 3'-single-stranded overhang 1002 the shortened pri-miR172a substrate. Such functional equivalence can be evaluated by re-hybridization with probes for the overhang regions 1001 and 1002. Such functional equivalence should produce results analogous to those presented in FIG. 13 and/or 14. As shown in FIG. 13, the digestive protein, represented by HIGLE, may remove or otherwise digest the 5'-overhang 1001 of the Y-junction of shortened pri-miR172a. Diminished presence of the signal provided by a probe for the 5'-overhang 1001 shown in FIG. 13 indicates that the overhang is generally not found following exposure to the digestive protein. Likewise, diminished presence of the signal provided by a probe for the 3'-overhang 1002 shown in FIG. 14 indicates that the overhang is generally not found following exposure to the digestive protein. The presence of the signal provided by the probe for the 3'-overhang 1002 mainly in the in the same region of the 100 nucleotide fragment may confirm functional equivalence with respect to potentiation of SE and/or HYL1 on digestion of double-stranded nucleic acids comprising at least one of a Y-junction and a bulge.

Figure 15:
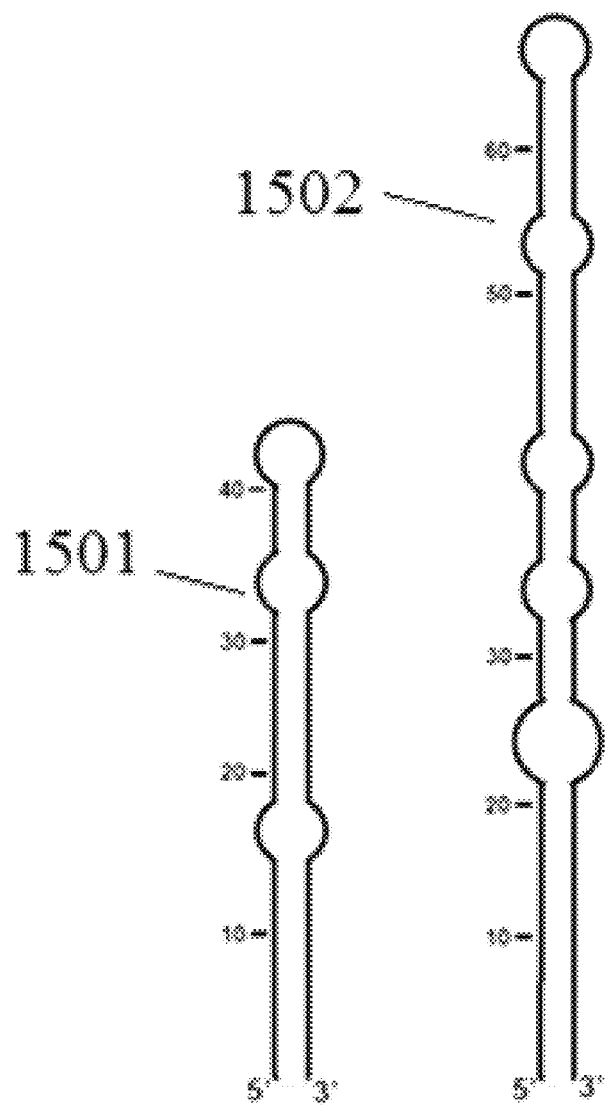
FIG. 15 is an illustration of pre-miRNA molecules that may be used to evaluate functional equivalence.

The digestive protein may be functionally equivalent to SEQ ID NO: 1 with respect to the pattern of cleavage of pre-miRNA molecules other than shortened pri-miR172a substrate. For example, the digestive protein may be functional equivalent with respect to the cleavage of pre-miR160a 1501 and/or pre-miR164b 1502, illustrated in FIG. 15. As illustrated in FIG. 15, pre-miR160a 1501 has three bulges and pre-miR164b has four bulges. Functional equivalence with respect to cleavage of pre-miR160a 1501 and/or pre-miR164b 1502 may be evaluated by labeling these RNAs through the incorporation of radioactively labeled UTP within their nucleotide sequence, and should provide results analogous to those shown in FIGS. 16 and 17. The signal provided by the labeled UTP enables analysis of the fragments provided following exposure to increasing concentrations of the digestive protein.

Figure 16:
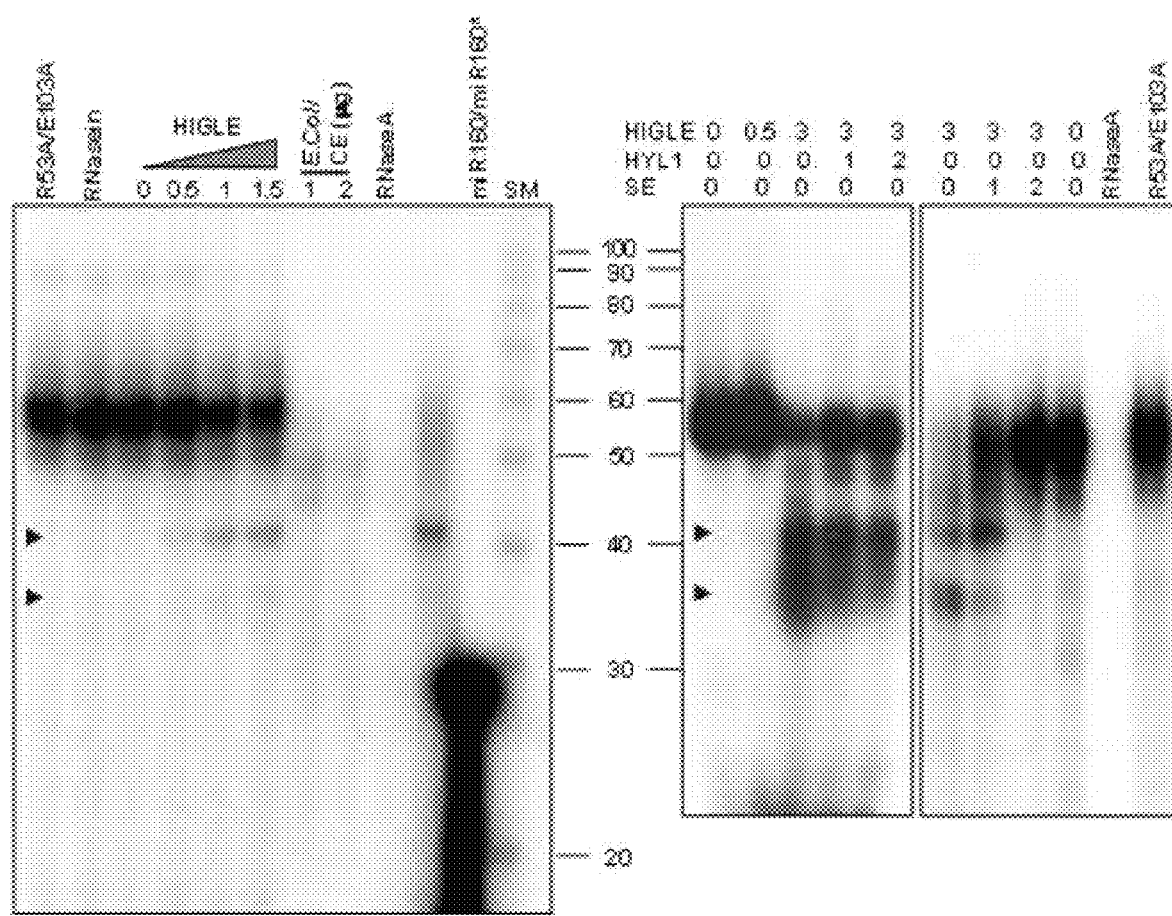
Figure 17:
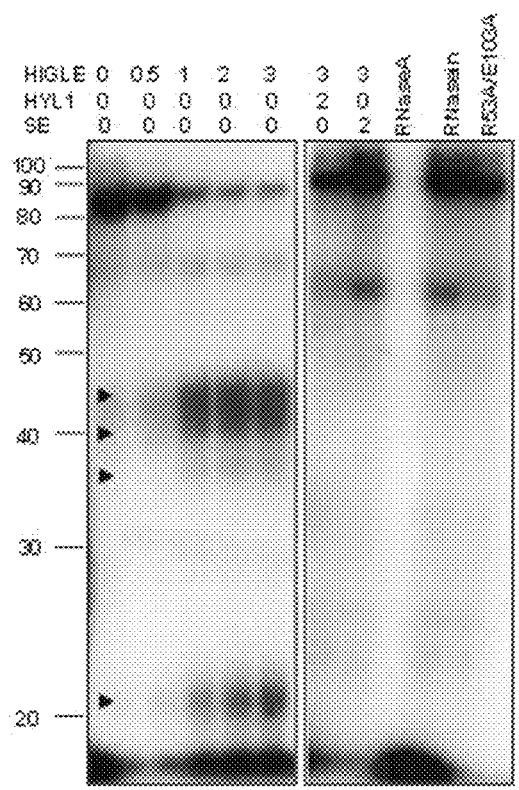
FIG. 17 shows results analogous of functional equivalence with respect to cleavage of pre-miR164b.

FIG. 16 shows the pattern of fragments provided UTP labeled pre-miR160a 1501 following exposure to 0 to 3.0× $10^{-8}$ g concentrations of a digestive protein, represented by HIGLE. Digestion into smaller fragments is observed with an increasing concentration of the digestive protein. FIG. 17 shows the results of a similar analysis conducted using UTP labeled pre-miR164b 1502.

As shown in FIG. 16, digestion of pre-miR160a by the digestive protein may provide two fragments of approximately 35 nucleotides and approximately 40 nucleotides in length. Digestion of pre-miR164b may provide five fragments, as shown in FIG. 17, with four of the fragments having lengths spanning approximately 35 nucleotides to approximately 50 nucleotides and a single fragment of approximately 20 nucleotides in length.

The digestive protein may be functionally equivalent to SEQ ID NO: 1 with respect to the pattern of cleavage of miR160a 1501 and/or pre-miR164b 1502 provided in the presence of HYL1 and/or SE. Such functional equivalence can be evaluated by digesting miR160a 1501 and/or pre-miR164b 1502 in the presence of HYL1 and/or SE, and should provide results analogous to those presented in FIGS. 16 and 17.

Removing double-stranded false positive nucleic acid strands comprising at least one of a Y-junction and a bulge can allow for more accurate detection of nucleic acids sequences, thereby enabling more accurate diagnosis and/or treatment. Detecting a nucleic acid strand corresponding to gene, mRNA of an expressed protein and/or miRNA may be accomplished by first creating a plurality of double-stranded nucleic acids by hybridizing a plurality of single-stranded nucleic acids within a sample with a plurality of probe nucleic acids. The sample may comprise RNA and/or DNA from cells or tissue. As to favor formation of double-stranded nucleic acids, the nucleic acids of the sample are preferably denatured (i.e. split apart into single strands). Single-stranded nucleic acid probes are allowed to bind to the sample single-single-stranded nucleic acids. Upon binding, a double-stranded nucleic acid comprising a first strand including one of the single-stranded nucleic acids of the plurality of single-stranded nucleic acids within the sample and second strand including one of the plurality of probe nucleic acids is formed. False positive can then be removed from the resulting plurality of double-stranded nucleic acids by exposing the plurality of double-stranded nucleic acids to a digestive protein capable of digesting at least one of the first strand and the second strand of a false positive double-stranded nucleic acids comprising at least one of a bulge and a Y-junction. Having removed the false positives, the remaining double-stranded nucleic acids can be detected to provide a more accurate analysis.

A nucleic acid strand, such as miRNA, mRNA, cDNA and/or DNA, is detected within the sample of single-stranded nucleic acids through the use of the probe. The probe contains a nucleic acid stand complimentary to the strand to be detected. This permits the probe to selectively bind to the nucleic acid to be detected, creating a double-stranded complex. Either the probe or the single-stranded nucleic acids within the sample may be labeled, so the presence of double-stranded nucleic acids can be detected. Single-stranded nucleic acids within the may be separated based on size using gel electrophoresis. A membrane may then be placed upon the gel. Clinging to the membrane, the single-stranded nucleic acids within the sample may be picked up from the gel when the membrane is removed. Depending on the affinity of the nucleic acids of the sample to the membrane used, it may be preferable to fix the sample to the membrane. After the single-stranded nucleic acids of the sample have been satisfactorily adhered to the membrane, the membrane may be exposed to labeled probes. Containing a specific sequence of nucleotides complimentary to the genes, cDNA, mRNA, miRNA, and/or DNA to be detected within the sample, the labeled probes selectively bind to the sample's single-stranded nucleic acids stuck on the membrane having a matching nucleotide sequence. When the probes bind to their match, a double-stranded nucleic acid results. However, a portion of the resulting double-stranded nucleic acids may be false positives comprising a bulge and/or Y-junction. At least a portion of these positive can be removed by exposing the double-stranded nucleic acids to a digestive protein functionally equivalent to SEQ ID NO: 1, or a portion thereof. After providing sufficient time for the digestive protein to find and remove the false positive double-stranded nucleic acids, the membrane may be washed to remove unbound probes and false positive fragments. The double-stranded nucleic acids containing the probes remaining on the membrane may then be detected using the probes' labels.

In addition to a membrane, the single-stranded nucleic acids to be detected may be fixed to slide or other such surface. Furthermore, it may not be necessary to extract the single-stranded nucleic acids from a sample. The sample containing the genes, RNA, mRNA, and/or miRNA to be detected may be adhered to a surface.

As to favor formation of double-stranded nucleic acids with the probe, the nucleic acids of the sample are preferably denatured into single strands. The surface may be exposed to labeled probes. When the probes bind to their matching single-stranded nucleic acids with the adhered sample, double-stranded nucleic acid results. After giving the probes sufficient time to find and bind to their match on the surface, false positive double-stranded nucleic acids may be removed by exposing the surface to the digestive protein and then washed to remove unbound probes and false positive fragments. The double-stranded nucleic acids containing the probes remaining on the surface may then be detected using the probes' labels.

The single-stranded nucleic acids of the sample may carry a label in addition to and/or instead of the probes. A sample comprising labeled singled-stranded nucleic acids may be created by extracting RNA from a cell and/or tissue to be analyzed. The extracted RNA may then be used create a labeled sample single-stranded cDNA through reverse transcription conducted using radioactive or other labeled nucleotides. In other instances, a labeled sample may be generated by creating labeled DNA copies of the cDNA using polymerase chain reaction (PCR) or other nucleotide amplification techniques with labeled nucleotides. The labeled single-stranded nucleic acids of the sample may then be exposed to probes fixed to a surface. The single-stranded nucleotides within the sample bind to matching probes, creating double-stranded nucleic acids. After giving the single-stranded nucleotides within the sample time to find and bind to their match on the surface, false positive double-stranded nucleic acids may be removed by exposing the surface to the digestive protein. The surface may then be washed to remove unbound strands from the sample and false positive fragments. The remaining double-stranded nucleic acids remaining on the surface may then be detected using the label.

The labels utilized may be in the form of the fluorescent markers that emit light. In other instances, the labels may be visible by x-ray analysis. The label may comprise sequence or molecules attached the probe and/or nucleic acids of the sample that permit binding of and/or formation of a complex with detectable proteins and/or molecules. Regardless, of how the labels are made visible, it is the presence of the label in double-stranded nucleic acids that is detected.

The label may promote enzymatic activity. For example, the label may promote selective amplification of single-stranded nucleic acids, so that an increase in the amount of strands may be used to detect the presence of double-stranded nucleic acids. Such detection may be accomplished by utilizing a PCR technique that selectively amplifies specific single-stranded nucleotides within the sample. During amplification, a DNA polymerase binds to single-stranded DNA and makes a complimentary copy of the strand. DNA polymerase, however, is incapable of binding to the strand on its own. The help of a primer is required. Accordingly, until a primer is present on a strand, DNA polymerase will not bind to or copy nucleic acid strands within the sample. As the presence of a primer controls DNA amplification, the primer may be itself a label. That is, the probe may contain a primer. When the probe finds its match within the sample, a double-stranded nucleic acid having the primer is created. Removal of false double-stranded nucleic acids having the primer may be accomplished by exposing double-stranded nucleic acids to the digestive protein during amplification. Such concurrent exposure may reduce and/or eliminate amplification by false positive double-stranded nucleic acids containing the primer label. The presence of the double-stranded nucleic acid can be detected by an amplification (i.e. an increase) in the amount of the nucleic acid sequence above a threshold value.

It should be understood that the effects of the inventive concepts are not limited to the above-described effects, and encompasses all types of effects deducible from the configurations of the exemplary embodiments disclosed in the detailed description and claims It should be understood by those skilled in the art to which the inventive concepts pertains that the description proposed herein is given for the purpose of illustration only, and various changes and modifications can be made to the above-described exemplary embodiments of the inventive concepts without departing from the scope of the invention. Accordingly, the exemplary embodiments of the inventive concepts are not intended to limit the scope of the invention but to describe the invention. For example, individual components described in an integral form may be implemented in a dispersed form, and individual components described in a dispersed form may also be implemented in an integral form.

The scope of the inventive concepts are defined by the appended claims, and encompasses all modifications and alterations derived from meanings, the scope and equivalents of the appended claims.

What is claimed is:

1. A method of detecting a nucleic acid sequence with reduced false positives, comprising:

creating a plurality of double-stranded nucleic acids by hybridizing a plurality of single-stranded nucleic acids within a sample with a plurality of probe nucleic acids, each double-stranded nucleic acid of the plurality of double-stranded nucleic acids comprising a first strand including one of the single-stranded nucleic acids of the plurality of single-stranded nucleic acids within the sample and second strand including one of the plurality of probe nucleic acids;

exposing the plurality of double-stranded nucleic acids to a digestive protein, the digestive protein comprising an amino acid sequence as set forth in SEQ ID NO:1 which (a) comprises a GIY-YIG motif, and (b) has a bifunctional nature based on RNA and DNA, wherein said exposure digests at least one of the first strand and the second strand of a double-stranded nucleic acid of the plurality of double-stranded nucleic acids comprising at least one of a bulge and a Y-junction resulting from mismatched double-stranded nucleic acids that form false positives;

washing the sample to remove unbound probes and false positive fragments following said exposure to the digestive protein; and detecting a presence of the plurality of double-stranded nucleic in the sample.

2. The method according to claim 1, wherein the GIY-YIG motif consists of the amino acid sequence set forth in SEQ ID NO: 2.

3. The method according to claim 1, wherein the GIY-YIG motif comprises:
- a GIY-sequence;
- a YIG-sequence; and
- a space spanning region between the GIY-sequence and the YIG-sequence, the space spanning region comprising a glycine residue.

4. The method according to claim 3, wherein the space spanning region consists of 10 to 11 amino acids.

* * * * *

SEQUENCE LISTING

```
<160> NUMBER OF SEQ ID NOS: 2

<210> SEQ ID NO 1
<211> LENGTH: 368
<212> TYPE: PRT
<213> ORGANISM: Arabidopsis thaliana

<400> SEQUENCE: 1

Met Arg Glu Lys Arg Gly Asn Arg Lys Ala Leu Asp Pro Val Gly Glu
1               5                   10                  15

Asp Gly Val Thr Gly Lys Asp Gly Lys Gly Phe Phe Ala Cys Tyr Leu
            20                  25                  30

Leu Thr Ser Leu Ser Pro Arg His Lys Gly Gln Thr Tyr Ile Gly Phe
        35                  40                  45

Thr Val Asn Pro Arg Arg Ile Arg Gln His Asn Gly Glu Ile Thr
    50                  55                  60

Ser Gly Ala Trp Arg Thr Lys Lys Arg Pro Trp Glu Met Val Leu
65                  70                  75                  80

Cys Ile Tyr Gly Phe Pro Thr Asn Val Ser Ala Leu Gln Phe Glu Trp
                85                  90                  95

Ala Trp Gln His Pro Arg Glu Ser Val Ala Val Arg Glu Ala Ala Ala
            100                 105                 110

Ala Phe Lys Ser Phe Ser Gly Val Ala Ser Lys Ile Lys Leu Val Tyr
        115                 120                 125

Thr Met Leu Asn Leu Pro Ala Trp Asn Ser Leu Asn Leu Thr Val Asn
    130                 135                 140

Tyr Phe Ser Ser Lys Tyr Ala His His Gly Gly Lys Ser Pro Ser Leu
145                 150                 155                 160

Pro Leu His Met Lys Val Gln Val Cys Ala Met Glu Asp Leu Gln Tyr
                165                 170                 175
```

```
Phe Thr Lys Val Asp Asp Ser Ser Gln Pro Glu Asp Glu Glu Ser Pro
            180                 185                 190

Glu Val Asn Glu Glu Asp Asp Asp Asp Asp Asp Asp Ser Ser Asn
        195                 200                 205

Leu Ser Gln Pro Gly Asn Ser Asn Thr Ser Ser Ser Asp Asp Arg His
        210                 215                 220

Phe Glu Lys Ala Lys Glu Pro Val Thr Val Phe Asp Glu Glu Asp Arg
225                 230                 235                 240

Leu Ala Asn Phe Ser Gly Phe Gly Leu Leu Asp Glu Glu Glu Thr Val
                245                 250                 255

Glu Asp Glu Val Ser His Ile Thr Val Gly Ser Ile Arg Ala Thr Glu
            260                 265                 270

Lys Glu Pro Glu Thr Val Phe Asn Asp Arg Leu Ala Ser Phe Thr Cys
            275                 280                 285

Phe Gly Leu Val Glu Ile Val Glu Asp Glu Val Ser His Gly Thr Ile
        290                 295                 300

Gly Ser Thr Glu Ala Met Glu Lys Glu Cys Arg Lys Arg Arg Asn His
305                 310                 315                 320

Ile Thr Ser Thr Thr Thr Glu Val Asp Val Glu Val Ile Asp Leu Met
                325                 330                 335

Thr Pro Ser Pro Ser Cys Arg Ala Gly Ser Ser Met Lys Arg Arg Arg
                340                 345                 350

Val Ser Glu Phe Ile Asp Leu Thr Met Ser Pro Asn Phe Ile Glu Ser
            355                 360                 365

<210> SEQ ID NO 2
<211> LENGTH: 87
<212> TYPE: PRT
<213> ORGANISM: Arabidopsis thaliana

<400> SEQUENCE: 2

Phe Phe Ala Cys Tyr Leu Leu Thr Ser Leu Ser Pro Arg His Lys Gly
1               5                   10                  15

Gln Thr Tyr Ile Gly Phe Thr Val Asn Pro Arg Arg Arg Ile Arg Gln
            20                  25                  30

His Asn Gly Glu Ile Thr Ser Gly Ala Trp Arg Thr Lys Lys Lys Arg
        35                  40                  45

Pro Trp Glu Met Val Leu Cys Ile Tyr Gly Phe Pro Thr Asn Val Ser
    50                  55                  60

Ala Leu Gln Phe Glu Trp Ala Trp Gln His Pro Arg Glu Ser Val Ala
65                  70                  75                  80

Val Arg Glu Ala Ala Ala Ala
                85
```